United States Patent [19]

Nishida et al.

[11] 4,011,277

[45] Mar. 8, 1977

[54] PREPARATION OF SQUALANE BY HYDROGENOLYSIS

[75] Inventors: Takashi Nishida; Yoichi Ninagawa; Kazuo Itoi, all of Kurashiki; Yutaka Omura; Haruo Nagai, both of Niigata, all of Japan

[73] Assignees: Kuraray Co., Ltd., Kurashiki; Kyowa Gas Chemical Industry Co., Ltd., Tokyo, both of Japan

[22] Filed: Mar. 25, 1974

[21] Appl. No.: 454,694

[30] Foreign Application Priority Data

| | | |
|---|---|---|
| Apr. 7, 1973 | Japan | 48-39667 |
| Apr. 26, 1973 | Japan | 48-48193 |
| Sept. 7, 1973 | Japan | 48-101416 |

[52] U.S. Cl. ............ 260/676 R; 260/632 R; 260/635 R; 260/635 M; 260/635 Y; 260/642 R; 260/683.9

[51] Int. Cl.² ............................................ C07C 9/14

[58] Field of Search ............ 260/676, 682, 683.9

[56] References Cited

UNITED STATES PATENTS

| | | | |
|---|---|---|---|
| 2,440,678 | 5/1948 | Ford et al. | 260/683.9 |
| 2,992,278 | 7/1961 | Tedeschi | 260/683.9 |
| 3,203,998 | 8/1965 | House et al. | 260/617 |
| 3,379,766 | 4/1968 | Hwang et al. | 260/676 |
| 3,501,546 | 3/1970 | Dubeck et al. | 260/676 |
| 3,794,692 | 2/1974 | Komatsu et al. | 260/677 |
| 3,801,668 | 4/1974 | Komatsu et al. | 260/677 |

FOREIGN PATENTS OR APPLICATIONS

| | | | |
|---|---|---|---|
| 734,431 | 8/1955 | United Kingdom | 260/683.9 |

OTHER PUBLICATIONS

Ann. of Chemistry, vol. 60, 1971.
Chem. Listy, vol. 50, pp. 569–572, 1956.
J.A.C.S., vol. 65, pp. 809–813, 1943.

*Primary Examiner*—Herbert Levine
*Attorney, Agent, or Firm*—Flynn & Frishauf

[57] ABSTRACT

Novel 2,6,10,15,19,23-hexamethyltetracosane-10,15-diol derivatives. Such derivatives are prepared by hydrogenation of 2,6,10,15,19,23-hexamethyltetracosa-11,13-diyne-10,15-diol derivatives and used as starting materials for preparing squalane.

12 Claims, No Drawings

PREPARATION OF SQUALANE BY HYDROGENOLYSIS

This invention relates to methods for the industrial preparation of squalane. More particularly, this invention relates to new intermediates for preparing squalane and new methods for preparing the same and squalane.

The intermediates according to this invention have the following formula (I):

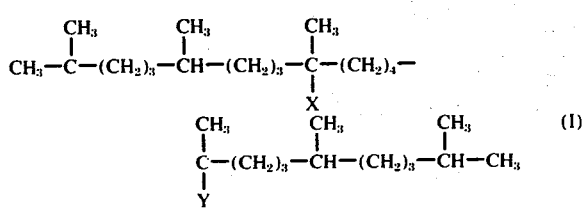

wherein both X and Y represent hydroxy radicals or one of X and Y represents a hydroxy radical and the other represents a hydrogen atom.

According to this invention, the intermediate can be prepared by the following methods:

a. a method which comprises reaction of a $C_{13}$-ketone having 13 carbon atoms represented by the following formula (II) (hereinafter referred to as $C_{13}$-ketone):

with diacetylene according to the usual method to obtain a 2,6,10,15,19,23-hexamethyltetracosa-11,13-diyne-10,15-diol derivative having the general formula (III) (hereinafter referred to as diacetylene diol):

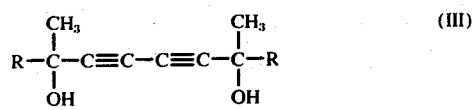

wherein R represents saturated or unsaturated hydrocarbon residues having 11 carbon atoms represented by the following carbon atom skeleton:

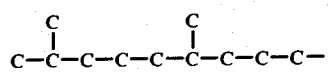

and both of R may be the same or different and hydrogenation of the above diacetylene diol (III).

b. a method which comprises oxydative coupling of a monoacetylene alcohol having the following formula (IV) (hereinafter referred to as monoacetylene alcohol)

wherein R is the same as above defined and hydrogenation of the resultant diacetylene diol having the general formula (III).

According to this invention, squalane can be prepared by the following methods using the intermediates (I) as starting materials:

c. a method which comprises dehydration and subsequent hydrogenation of the intermediates (I).

d. hydrogenolysis of the intermediates (I).

Therefore, an object of this invention is to provide an industrial peparation of squalane.

A further object of this invention is to obtain squalane in low costs and industrial scale.

Another object of this invention is to provide the new intermediates (I) for preparing squalane.

A still further object of this invention is to provide methods for preparing the intermediates (I).

A particular object of this invention is to provide new methods for preparing the intermediates (I) using usually available substances as starting materials by the usual method.

All other objects of this invention will in part be obvious from the contents of the specification hereinafter disclosed.

As is known, squalane, 2,6,10,15,19,23-hexamethyltetracosane is used as additive or base of several cosmetics because of its characteristics of cleaning action for skin and its penetrating action to skin. Also it is a useful material as a lubricant for precision machines. It has now been prepared by hydrogenation of the squalene portion obtained from shark's liver oil; its preparation using industrial products as starting material has almost never been tried.

According to this invention, squalane can be prepared:

c. by dehydration and subsequent hydrogenation of the intermediates (I); or d. by hydrogenolysis of the intermediates (I).

Therefore, the methods for preparing the intermediates (I) will be described in detail in the first place.

As has been already described, the intermediates (I) can be prepared: by the method (a) which comprises reaction of the $C_{13}$-ketone (II) having the following formula

wherein R is the same as above defined with diacetylene and hydrogenation of the resultant diacetylene diol (III) having the general formula:

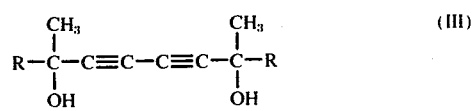

wherein R is the same as above defined or by the method (b) which comprises oxydative coupling of the monoacetylene alcohol (IV) having the general formula:

wherein R is the same as above defined and hydrogenation of the diacetylene diol (III).

$C_{13}$ ketones (II) which may be used industrially and usefully are, for example, geranyl acetone, hexahydropseudoionone, 6,10,-dimethylundeca-5,10-dien-2-one, pseudoionone, citronellidene acetone, dihydrocitronellidene acetone et al. These ketones can be prepared in industrial scale and at a comparative low price by the following methods. For example, geranyl acetone can be prepared industrially by Carroll rearrangement reaction of linallol with acetoacetic acid ester. Hexahydropseudoionone can be easily obtained by hydrogenation of geranyl acetone or pseudoionone. 6,10-Dimethylundeca-5,10-dien-2-one can be easily prepared by partial hydrogenation of 3,7-dimethylocta-7-en-1-yn-3ol obtained by the method of W. Hoffmann et al. (Ann. 747 60 (1971)) to 3,7-dimethylocta-1,7-dien-3-ol and then by Carroll rearrangement reaction of the resultant with acetoacetic acid ester in the same manner as in linallol. Psuedoionone, citronellidene acetone and dihydrocitronellidene acetone can be prepared respectively by aldol condensation of citral, citronellal and tetrahydrocitral with acetone.

Diacetylene which is reacted with the $C_{13}$-ketone (II) has never been used usefully and has been thrown away as a by-product in acetylene preparation; so it can be available at a low price.

Diacetylene may be used in a comparative pure state without isolation of pure diacetylene.

The monoacetylene alcohols (IV) can be prepared by the reaction of the $C_{13}$-ketone (II) with acetylene, which will be described in detail hereinafter. By ethynylation of several compounds (II) with acetylene, the corresponding compounds (IV) can be prepared; but industrially available compounds (IV) are preferred. For example, 3,7,11-trimethyldodeca-6,10-dien-1-yn-3-ol, 3,7,11-trimethyldodeca-6,11-dien-1-yn-3-ol and 3,7-trimethyl dodeca-1-yn-3-ol can be easily prepared by ethynylation of geranyl acetone, 6,10-dimethylundeca-5,10-dien-2-one and hexahydropseudoionone respectively with acetylene. And these compounds are preferred compounds among the compounds (IV) according to this invention.

Upon reaction of the compounds (II) with diacetylene, known methods for preparing acetylene alcohols can be applied broadly. The preferred methods according to this invention are as follows: (1) the method of reaction of the compounds (II) with Grignard compound of diacetylene in such a solvent as diethyl ether which is used in the general Grignard reaction; (2) the method of reaction of the compounds (II) with diacetylide made by passing diacetylene into the liquid ammonia solution made by dissolving alkaline metal or alkaline earth metal such as lithium, sodium, potassium or calcium in liquid ammonia; (3) the method of reaction of the compounds (II) with diacetylene in the presence of a alkali metal in liquid ammonia or in an organic solvent, for example, the reaction of (II) with diacetylene in the presence of potassium hydroxide or sodium amide and the like in such a solvent as ether or tetrahydrofuran.

Upon oxydative coupling reaction of the compounds (IV), known oxydative coupling reaction can be applied broadly. The preferred methods according to this invention are as follows: (4) the method comprising adding a solution of the compound (IV) in such a solvent soluble in water as ethanol, acetone or tetrahydrofuran to an aqueous solution of monovalent copper salt such as cuprous chloride and ammonium chloride and oxydative coupling of the compound (IV) in an oxygen atmosphere; (5) the method comprising adding the compound (IV) to a solution of a monovalent copper salt such as cuprous chloride in a solvent such as pyridine or picoline and oxydative coupling of the compound in an oxygen atmosphere; (6) the method comprising adding the compound (IV) to a solution of bivalent copper salt such as cupric acetate in a solvent such as pyridine or picoline.

In the above method (4), a small amount of hydrochloric acid, cupric chloride or ammonia may be added to this system for promotion of the reaction. Also in the above method (6), a reaction promoting agent such as tetramethylethylenediamine may be added and a mixture of pyridine with methanol, ether or acetone may be used.

Representatives of the compounds having formula (III) according to this invention are as follows:

1. 2,6,10,15,19,23-hexamethyltetracosa-2,6,18,22-tetraene-11,13-diyne-10,15-diol
2. 2,6,10.15,19,23-hexamethyltetracosa-18,22-diene-11,13-diyne-10,15-diol 3. 2,6,10,15,19,23-hexamethyltetracosa-1,6,18,22-tetraene-11,13,-diyne-10,15-diol
4. 2,6,10,15,19,23-hexamethyltetracosa-2,6,8.18,22-pentaene-11,13-diyne-10,15-diol
5. 2,6,10,15,19,23-hexamethyltetracosa-2,8,18,22-tetraene-11,13-diyne-10,15-diol
6. 2,6,10,15,19,23-hexamethyltetracosa-8,18,22-triene-11,13-diyne-10,15-diol
7. 2,6,10,15,19,23-hexamethyltetracosa-11,13-diyne-10,15-diol
8. 2,6,10,15,19,23-hexamethyltetracosa-1,6-diene-11,13-diyne-10,15-diol
9. 2,6,10,15,19,23-hexamethyltetracosa-2,6,8-triene-11,13-diyne-10,15-diol
10. 2,6,10.15,19,23-hexamethyltetracosa-2,8-diene-11,13-diyne-10,15-diol
11. 2,6,10,15,19,23-hexamethyltetracosa-8-ene-11,13-diyne-10,15-diol
12. 2,6,10,15,19,23-hexamethyltetracosa-1,6,18,23-tetraene-11,13-diyne-10,15-diol
13. 2,6,10,15,19,23-hexamethyltetracosa-2,6,8,18,23-pentaene-11,13-diyne-10,15-diol
14. 2,6,10,15,19,23-hexamethyltetracosa-2,8,18,23-tetraene-11,13-diyne-10,15-diol
15. 2,6,10,15,19,23-hexamethyltetracosa-8,18,23-triene-11,13-diyne-10,15-diol
16. 2,6,10,15,19,23-hexamethyltetracosa-2,6,8,16,18,22-hexaene-11,13-diyne-10,15-diol
17. 2,6,10,15,19,23-hexamethyltetracosa-2,8,16,18,22-pentaene-11,13-diyne-10,15-diol
18. 2,6,10,15,19,23-hexamethyltetracosa-8,16,18,22-tetraene-11,13-diyne-10,15-diol
19. 2,6,10,15,19,23-hexamethyltetracosa-2,8,16,22-tetraene-11,13-diyne-10,15-diol
20. 2,6,10,15,19,23-hexamethyltetracosa-8,16,22-triene-11,13-diyne-10,15-diol
21. 2,6,10,15,19,23-hexamethyltetracosa-8,16-diene-11,13-diyne-10,15-diol The diacetylene diol compounds (III) give the compounds (I) or a mixture of the compounds (I) and squalane upon hydrogenation. For this hydrogenation a usual method can be available. As catalysts, for example, palladium, platinum, rhodium, ruthenium, iridium, osmium or these metal oxides, nickel, and cobalt may be used. The above catalysts may be used in a form supported on a carrier. Preferred catalysts are those such as palladium or platinum supported on active carbon, Raney nickel, and Raney cobalt. In case of preparation of the compounds (I) from the compounds (III), the compounds (III) may contain the compounds (II) or (IV) as unreacted materials which are used on the occasion of preparation of the compounds (III).

As solvents used upon hydrogenation of the compounds (III), for example, broad materials consisting of carbon, hydrogen and oxygen atoms such as hydrocarbons, alcohols, ethers, ketones, organic esters, and organic carboxylic acids may be used. It is desirable to avoid using solvents which are easily subjected to hydrogenation under the conditions of hydrogenation of the compounds (III).

Hydrogenation can be carried out under a hydrogen pressure of 1 to 120 kg/cm$^2$. Hydrogenation temperature is depending on a sort of a catalyst and a hydrogen pressure. It can be carried out at a temperature over room temperature, but preferably in the range of 60° – 200°C.

The hydrogenation products of the compounds (III) usually consist of a mixture of 10,15-dihydroxysqualane (V) (2,6,10,15,19,23hexamethyltetracosane-10,15-diol),10-hydroxysqualane(VI) (2,6,10,15,19,23-hexamethyltetracosan-10-ol) and squalane and the composition mainly varies according to catalysts, solvents and reaction temperatures in case of hydrogenation and also according to a concentration of catalyst used. But this variation of composition does not act upon any great effect against subsequent steps; so a mixture of the compounds (V), (VI) and squalane in a optional ratio may be subjected to subsequent treatments.

Next, squalane can be prepared by dehydration of the compounds (I) which may be a mixture with squalane and by subsequent hydrogenation of the dehydration products. Dehydration of the compounds (I) can be carried out in a suitable solvent or in no solvent in the presence of a suitable acidic catalyst: a Bronsted acid such as sulfuric acid, or phosphoric acid; a Lewis acid such as zinc chloride, aluminum chloride, boron trifluoride or stannic chloride; a solid acid such as alumina, active silica, silica-alumina, solid phosphoric acid or cation exchange resin. In case of using, for example, mineral acids such as sulfuric acid and phosphoric acid, Lewis acids such as zinc chloride and aluminium chloride and solid acids such as cation exchange resin as catalyst, the dehydration can be carried out almost in quantitative yield under mild conditions, for example, at temperatures of about 100°C in an organic solvent, preferably, in a hydrocarbon, primary alcohol, ether and ketone or in no solvent; in case of using solid acids such as alumina, silica-alumina and active silica as catalyst, it is preferred to use higher temperatures of 180°~250°C to complete the dehydration in short time.

Upon hydrogenation of the above dehydration products, usual hydrogenation methods may be applied in the same manner as in case of hydrogenation of the compounds (III). Catalysts and solvents used can be optionally selected from the same scope as used in case of hydrogenation of the compounds (III). Reaction temperatures, catalyst concentration and hydrogen pressures can be varied in a broad scope; the hydrogenation can be carried out preferably at temperatures of 0°~300°C and under hydrogen pressures of 1~200 kg/cm$^2$. The product, squalane can be easily separated and recovered by means of usual separation treatments containing distillation.

Another method for preparing squalane from the compounds (I), as above described, consists of hydrogenolysis of the compounds (I) which may be a mixture of the compounds (V), (VI) and/or squalane. Hydrogenolysis can be carried out at higher temperatures by adding an acidic material to the usual hydrogenation systems. The catalysts used to the hydrogenolysis are metal catalysts such as nickel, cobalt, palladium, platinum, rhodium, iridium, ruthenium, osmium and rhenium or these metal compounds or catalysts in which these catalysts are supported on a suitable carrier. The hydrogenolysis using such as catalysts can be carried out by several kinds of methods, for example, by the following method:

1. the method being carried out in an organic carboxylic acid. Organic carboxylic acids used for this method are preferred to be acetic acid, propionic acid, lactic acid or isolactic acid. These acids can be used in combination with a higher acidic acid such as α-halogenated fatty acid or α-hydroxy fatty acid.

2. the method being carried out in an organic acid together with a small amount of a stronger acidic substance than the acidity of organic acid of which amount is not enough to prohibit the reaction. Acidic substances used are preferred to be: Brønsted acids such as boric acid, hydrochloric acid, sulfuric acid, phosphoric acid, and perchloric acid; Lewis acids such as zinc chloride, aluminum chloride, boron trifluoride, and titanium tetrachloride; solid acids such as activated alumina, silica-alumina, and solid phosphoric acid; hydrogen salts such as sodium hydrogen sulfate, sodium hydrogen carbonate, sodium hydrogen phosphate, and potassium hydrogen sulfate; salts of a strong acid and a weak base such as magnesium sulfate, calcium sulfate, barium sulfate, aluminium sulfate, copper sulfate, zinc sulfate, calcium chloride, magnesium chloride, and zinc nitrate.

3. the method being carried out in an organic solvent used for hydrogenation of the compounds (III), adding further an acid substance or an organic substance which both can be used in the method (2). But depending upon the reaction conditions, aromatic hydrocarbons, cyclic ethers, esters, ketones, alcohols (especially tertiary alcohol) are preferred to be avoided, because these solvents are apt to cause hydrogenation, ring-opening, hydrolysis, dehydration, and the like according to the conditions used.

4. the method being carried out in an organic solvent used in the method (3) in the presence of a catalyst, as described above, supported on a solid acid such as alumina, silica-alumina, or alumina-magnesia.

These methods for hydrogenolysis are preferred to be carried out in liquid phase at higher temperatures. The reaction temperature is preferred to be over about 100°C especially at temperatures from 150° to 300°C from the point of view of the reaction rate. This reaction can be carried out at atmospheric hydrogen pressure but it is preferred to be carried out at elevated hydrogen pressure especially at hydrogen pressures of about 20~150 kg/cm$^2$. An amount of catalyst used varies with a kind of the catalysts, but it is generally in the broad range of about 0.1~10%/w against the weight amount of the compounds (I).

The following examples are given to further illustrate the present invention. The scope of the invention is not, however, meant to be limited to the specific details of the examples.

EXAMPLE 1

In a 2-l three-necked and round-bottomed flask 1,000 ml of liquid ammonia and 11.5 g of metallic sodium were placed and diacetylene diluted with hydrogen containing about 30 mol % in the total sum of acetylene, methylacetylene and vinyl acetylene against diacetylene was passed thereinto. Then the solution of sodium in liquid ammonia changed from blue-green to white. At that time, 97.0 g of geranyl acetone was added thereto and the mixture was reacted under reflux of ammonia for 4 hours. After completion of the reaction, the liquid ammonia was distilled off by adding 54 g of ammonium chloride. To the residue 500 ml of ethyl ether and 500 ml of water were added. After decantation, the organic layer was washed with water and distilled off to give 121 g of a crude product.

The crude product was identified as 2,6,10,15,19,23-hexamethyltetracosa-2,6,18,22-tetraene-11,13-diyne-10,15-diol by means of a gel permeation chromatography made by Waters Co., Ltd. using as standard sample the compound prepared by the method of Reference 1 (Japanese patent Application No. 32274/1973; Filing date, Mar. 19, 1973) and found that the yield is 50.6% by means of calibration of its content using the standard sample.

A portion of 12.1 g of the above crude product was dissolved in 121 ml of acetic acid and 1.21 g of 5% Pd on active carbon and 1.21 ml of 3N—HCl were added thereto and the mixture was subjected to hydrogenolysis at 150°C under a hydrogen pressure of 1 kg/cm² to give 5.3 g of squalane, a fact which confirmed that the product of the above ethynylation reaction is 2,6,10,15,19,23-hexamethyltetracosa-2,6,18,22-tetraene-11,13-diyne-10,15-diol.

EXAMPLE 2

The reaction was carried out in the same manner as in Example 1 except that 6,10-dimethyldodeca-5,10-dien-2-on was used in place of geranyl acetone and 124 g of a crude product was obtained. The crude product was subjected to gel permeation chromatography by using as standard sample 2,6,10,15,19,23-hexamethyltetracosa-1,6,18,23-tetraene-11,13-diyne-10,15-diol prepare by the method of Reference 3 which was described in the same patent appliation as Reference 1 and was confirmed that 49.9 g of the crude product was 2,6,10,15,19,23-hexamethyltetracosa-1,6,18,23-tetraene-11,13-diyne-10,15-diol.

EXAMPLE 3

6,10-Dimethylundecan-2-one was reacted in place of geranyl acetone in the same manner as in Example 1 to give 120 g of a crude product. The crude product was subjected to gel permeation chromatography by using as standard sample 2,6,10,15,19,23-hexamethyltetracosa-11,13-diyne-10,15-diol prepared by the method of Reference 2 which was described in the same patent application as Reference 1 and was confirmed that 44.2 g of the crude product was 2,6,10,15,19,23 -hexamethyltetracosa-1,6,18,23-tetraene-11,13-diyne-10,15-diol.

Reference 1

In a 5-l. three-necked, and round-bottomed flask were placed 114.7 g of 3,7,11-trimethyldodeca-6,10-dien-l-yne-3-ol, 305.9 g of ammonium chloride, 765 ml of water and 76.5 ml of ethyl alcohol and the mixture was stirred at a room temperature by passing oxygen for 18 hours. After completion of the reaction, no starting material remained. The reaction mixture was centrifuged and was extracted with benzene. The organic layer was distilled off to remove benzene and ethyl alcohol. The residue was dissolved in benzene and washed with water. The benzene solution was dried over anhydrous calcium sulfate and the solid material was filtered off. The benzene solution thus obtained was distilled off to give 107.8 g of 2,6,10,15,19,23-hexamethyltetracosa-2,6,18,22-tetraene-11,13-diyne-10,15-diol as viscous liquid. A 3 g of this substance was further dissolved in 10 ml of benzene, treated with active carbon and purified by distilling the benzene.

Reference 2

In a 1-l. three-necked and round-bottomed flask were placed 10.5 g of 3,7,11-trimethyldodeca-l-yne-3ol, 5.0 g of ammonium chloride, 12.0 g of tetramethylethylenediamine and 675 ml of pyridine. The mixture was reacted at temperatures of 50° – 55°C for 6 hours under an oxygen atmosphere. After completion of the reaction, the alcohol as a starting material was not detected. After distillation of pyridine from the reaction mixture, 300 ml of benzene and 200 ml of water were added to the residue and after decantation, the organic layer was washed with 3N—H₂SO₄ and then water and dried. The benzene solution was distilled off to give 8.55 g of 2,6,10,15,19,23-hexamethyltetracosa-11,13-diyne-10,15-diol as viscous liquid. This compound was treated with active carbon and purified in the same manner as in reference 1.

Reference 3

This example was worked out in the same manner as in reference 2 except that 10.1 g of 3,7,11-trimethyldodeca-6,11-dien-l-yne-3-ol was used in place of 3,7,11-trimethyldodeca-l-yne-3-ol and 8.34 g of 2,6,10,15,19,23-hexamethyltetracosa-1,6,18,23-tetraene-11,13-diyne-10,15-diol was thus obtained. This compound was treated with active carbon and purified in the same manner as in reference 1.

EXAMPLE 4

In a 5-l three-necked and round-bottomed flask were placed 114.7 g of 3,7,11-trimethyldodeca-6,10-dien-l-yn-3-ol, 305.9 g of ammonium chloride, 191.2 g of cuprous chloride, 765 ml of water and 765 ml of ethyl alcohol and the mixture was stirred at room temperature for 18 hours by passing oxygen thereinto. After completion of the reaction there remained no unreacted starting material. The reaction mixture was centrifuged and the mother liquid was extracted with benzene. The benzene and ethyl alcohol were distilled off the organic layer and the residue was dissolved in benzene and washed with water. The benzene layer was dried over anhydrous calcium sulfate and the solid material was filtered off. The benzene was distilled off the benzene layer to give 107.8 g of crude 2,6,10,15,19,23-hexamethyltetracosa-2,6,18,22-tetraene-11,13-diyne-10,15-diol. A 107.8 g of the above diol, 50 ml of ethyl alcohol and 2.5 g of 5% Pd on active carbon were placed in an autoclave and the mixture was hydrogenated at 100° C under a hydrogen pressure of 3 – 5 kg/cm² until the absorption of hydrogen stopped. The obtained product consisted of a composition of the compounds (V), (VI) and squalane in the ratio of 84.9 : 14.6 : 0.5% respectively. The catalyst of Pd/C was filtered off and washed with 450 ml of ethyl alcohol. 14 ml of sulfuric acid was added to the combined ethylalcohol solution consisting of about 500 ml. The mixture was subjected to dehydration at 100° C for 2 hours. After cooling 300 ml of water was added to the reaction mixture and the ethyl alcohol was distilled off and the residue was extracted with benzene. The benzene layer was washed with water and dried over anhydrous sodium sulfate. 2.5 g of 5% palladium on active carbon was added to the solution and the mixture was subjected to hydrogenation at 50° C under a hydrogen pressure of 3 ~ 5 kg/cm². After the hydrogenation absorption stopped, the reaction mixture was cooled and the catalyst of Pd/C was filtered off and the benzene was distilled off to afford 78.8 g of a crude squalane. This crude squalane was distilled under reduced pressure to give 68.9 g of purified squalane having the boiling point range of 190° ~ 195°C/0.5 mmHg.

EXAMPLE 5

In a 1-l three-necked and round-bottomed flask 10.5 g of 3,7,11-trimethyldodeca-1-yne-3-ol, 5.0 g of cuprous chloride, 12.0 g of tetramethylethylenediamine and 675 ml of pyridine were placed and the mixture was subjected to oxydative coupling reaction at 50° ~ 55° C for 6 hours under an oxygen atmosphere. After completion of the reaction, there remained no unreacted starting alcohol. The pyridine was distilled off the reaction system and 300 ml of benzene and 200 ml of water were added to the residue and decanted. The organic layer was washed with 3N—$H_2SO_4$ and water, and dried. The benzene was distilled off to afford 8.55 g of 2,6,10,15,19,23-hexamethyltetracosa-11,13-diyne-10,15-diol. A 5.0 g portion of this product was dissolved in 10 ml of n-hexane and 0.25 g of 3% palladium on active carbon was added thereto. The mixture was subjected to hydrogenation at a temperature of 60° C of under a hydrogen pressure of 3 ~ 5 kg/cm² to give 4.6 g of the product consisting of the compounds (V) and (VI) in the ratio of 95.0 : 5.0% respectively.

EXAMPLE 6

The reaction was carried out in the same manner as in example 5 except that 10.1 g of 3,7,11-trimethyl-dodeca-6,11-dien-1-yn-3-ol was used in place of 3,7,11-trimethyldodeca-1-yn-3-ol and 8.34 g of 2,6,10,15,19,23-hexamethyltetracosa-1,6,18,23-tetraene-11,13-diyne-10,15-diol was obtained. 5 ml of ethyl alcohol and 0.5 g of W-5 type Raney nickel was added to 5.0 g of this product and it was hydrogenated at 100° C under a hydrogen pressure of 50 ~ 60 kg/cm² to give 4.5 g consisting of the compound (V) containing a small amount of the compound (VI).

EXAMPLE 7

In a 2-l round-bottomed flask was placed 1,000 ml of liquid ammonia, 23 g of sodium was dissolved thereinto and then 25 g of liquified diacetylene was added thereto. After stirring for 30 minutes, 388 g of geranyl acetone was added to the mixture and subjected to reaction under reflux of liquid ammonia. 80 g of ammonium chloride was added gradually to cause the ammonia to evaporate. 500 ml of benzene and 500 ml of water were added to the residue and decanted. The organic layer was repeatedly washed with water until the washed water became neutral and dried over anhydrous sodium sulphate and filtered. 20 g of 5% palladium on active carbon was added to the filtrate and it was hydrogenated at 50° C under a hydrogen pressure of 3 ~ 5 kg/cm². After completion of the reaction, the palladium catalyst was filtered off and the benzene was distilled off from the filtrate. The residue was distilled off under a reduced pressure of 0.5 mmHg to give 167 g of distillate containing hexahydropseudoionone as a main component, which was distilled below 90° C, and 194 g of the distilled residue. 8 g of zinc chloride was added and the mixture was subjected to reaction at 150° C for 30 mm, and 400 ml of n-heptane was added and washed with water and dried over anhydrous sodium sulfate. 10 g of 5% palladium on carbon was added to this n-heptane solution and the solution was hydrogenated at 50° C under a hydrogen pressure of 3 ~ 5 kg/cm². After completion of the reaction the catalyst was removed and the n-heptane was distilled off to give 162 g of a crude product. This product was distilled under reduced pressure to give 120 g of squalane having b.p. 190° ~ 195° C/0.5 mmHg.

EXAMPLE 8

The ethynylation reaction with diacetylene was carried out in the same manner as in example 7 except that 396 g of hexahydropseudoionone was used in place of geranyl acetone and a benzene solution of the product was hydrogenated in the same manner as in example 7 and then the product was subjected to dehydration, hydrogenation and distillation to give 91 g of squalane.

EXAMPLE 9

The ethynylation with diacetylene was carried out in the same manner as in example 8 except that 388 g of 6,10-dimethylundeca-5,10-diene-2-on was used in place of geranylacetone, and the product obtained was subjected to hydrogenation, dehydration and hydrogenation in the same manner as in example 8 and 112 g of squalane was obtained by distillation of the product.

EXAMPLE 10

To 100 ml of n-heptane was dissolved 50 g of 2,6,10,15,19,23-hexamethyltetracosa-11,13-diyne-10,15-diol which was prepared in the same manner as in example 5 and 2.5 g of 3% palladium on active carbon was added. The mixture was hydrogenated at 50° C under a hydrogen pressure of 3 ~ 5 kg/cm². The product was subjected to dehydration, hydrogenation and distillation in the same manner as in example 4 to give 40.6 g of squalane.

EXAMPLE 11

To 500-ml glass autoclave with a stirrer was placed a solution of 2 g of potassium hydroxide and 5 g of methanol and 200 ml of liquid ammonia was added thereinto under cooling to −78° C and diacetylene gas was passed thereinto until its amount reached to 5.0 g and then 70 g of hexahydropseudoionone was added thereto. Under stirring the inner temperature was caused to raise gradually and the mixture was stirred at temperatures of 10° ~ 15° C for 30 minutes so that the inner pressure raised to 6.5 kg/cm². After removal of ammonia at 15° C under reduced pressure, 300 ml of n-heptane was added to the residue and the solution was washed with water several times to remove the alkaline substance. The heptane layer with pale red-brown colour was separated and subjected to liquid chromatography and gas chromatography to determine the content of reaction product.

The results showed that 43 g of 2,6,10,15,19,23-hexamethyltetracosa-11,13-diyne-10,15-diol, object compound was formed and in addition 0.8 g of 5,9,13-trimethyltetradeca-1,3-diyne-5-ol was formed. There remained 30 g of hexahydropseudoionone which was unreacted. Therefore, the object compound was obtained in good yield from the starting material, hexahydropseudoionone.

A heptane solution of the object product was subjected to hydrogenation, dehydration and distillation in the same manner as in example 7 to obtain squalane.

EXAMPLE 12

In the identical autoclave as used in example 11, 5 g of a methanol solution containing potassium hydroxide 0.8 g was placed and, under cooling to −78° C, 200 ml of liquid ammonia was added thereto. Under cooling diacetylene gas was passed thereinto until its amount reached to 5.0 g. Then 59 g of geranyl acetone was added thereto, and under stirring the inner temperature was caused to raise and the mixture was stirred at 10° C for 30 minutes. After completion of the reaction the ammonia was removed at 15° C under reduced pressure and 300 ml of n-heptane was added, and the mixture was washed with water several times until the alkali was washed out. 5 g of palladium on carbon was added to the heptane layer with red-brown colour and hydrogen gas was passed thereinto with stirring for 2 hours under atmospheric pressure. After filtration of the catalyst the reaction solution was pale yellow and subjected to gas chromatography to analyse the reaction product. The results showed that the reaction product contained 42 g of 2,6,10,15,19,23-hexamethyltetracosane-10,15-diol, 1 g of 2,6,10,15,19,23-hexamethyltetracosan-10-ol, 1 g of 5,9,13-trimethylheptadecan-5-ol and 19 g of hexahydropseudoionone, which is the hydrogenation product of unreacted geranyl acetone. So the object compound was obtained in good yield from geranyl acetone. This reaction product was further subjected to dehydration and hydrogenation to afford squalane.

EXAMPLE 13

The reaction was carried out in the same manner as in example 12 except that 74 g of 6,10-dimethylundeca-5,10-dien-2-one was used in place of 59 g of geranyl acetone and the reaction product containing 41 g of 2,6,10,15,19,23-hexamethyltetracosane-10,15-diol, 1 g of 2,6,10,15,19,23-hexamethyltetracosan-10-ol, 1 g of 5,9,13-trimethylheptadecan-5-ol and 35 g of hexahydropseudoionone, which is the hydrogenation product of unreacted 6,10-dimethyldodeca-5,10-dien-2-one was obtained. This reaction product was subjected to hydrogenation, dehydration and hydrogenation in the same manner as in example 7.

EXAMPLE 14

In a 300-ml autoclave were placed 60 g of 2,6,10,15,19,23-hexamethyltetracosa-2,6,18,22-tetraene-11,13-diyne-10,15-diol, 120 ml of n-heptane and 3.0 g of 5% palladium on active carbon and the mixture was hydrogenated at 100° C under a hydrogen pressure of 50 kg/cm² for 5 hours. The catalyst was filtered off from the reaction mixture and the n-haptane was distilled off to give 59.4 g of a viscous raw product, which was distilled to afford 42.2 g of the purified product having b.p. 214° − 8° C/0.1 mmHg. This product was confirmed to be an unmixed substance by means of gas chromatography and liquid chromatography, and its structure was confirmed to be 2,6,10,15,19,23-hexamethyltetracosane-10,15-diol by means of infrared spectra, NMR spectra and Mass spectra. Elementary analyses for $C_{30}H_{62}O_2$ are as follows:

Calculated: C, 79.22; H, 13.72; O, 7.04. Found: C, 79.44; H, 13.70; O, 6.97.

Then in 300 ml autoclave were placed 20 g of the distilled 2,6,10,15,19,23-hexamethyltetracosane-10,15-diol, 40 ml of glacial acetic acid and 1 g of 5% palladium on active carbon and the mixture was hydrogenated at 200° C under a hydrogen pressure of 100 kg/cm² for 10 hours. The catalyst was filtered off, the reaction mixture and the acetic acid was distilled off to afford squalane in 100% conversion ratio, which was distilled through a packed column to give 14.2 g of the purified squalane.

EXAMPLE 15

In a 100 ml autoclave were placed 10 g of 2,6,10,15,19,23-hexamethyltetracosa-1,6,18,23-tetraene-11,13-diyne-10,15-diol, 20 ml of methanol and 0.5 g of 5% palladium on active carbon and the mixture was hydrogenated at 100° C under a hydrogen pressure of 100 kg/cm² for 18 hours. The obtained product consisted of 18.6% of squalane, 58.8% of 2,6,10,15,19,23-hexamethyltetracosan-10-ol and 30.6% of 2,6,10,15,19,23-hexamethyltetracosane-10,15-diol. Afer adding 0.2 ml of a 3N—HCl aqueous solution and 1 g of 5% palladium on active carbon, this product was hydrogenated at 200° C under a hydrogen pressure of 50 kg/cm² for 20 hours to give 7.6 g of squalane.

EXAMPLE 16

In a 100 ml autoclave were placed 10 g of 2,6,10,15,19,23-hexamethyltetracosa-11,13-diyne-10,15-diol, 20 ml of ethyl alcohol and 1 g of W-5 type Raney nickel and the mixture was hydrogenated at 100° C under a hydrogen pressure of 50 ~ 60 kg/cm² for 18 hours to give 2,6,10,15,19,23-hexamethyltetracosane-10,15-diol. The catalyst was filtered off and 1 g of Ni-catalyst supported on diatomaceous earth and 1 g of activated alumina were added to the filtrate, and it was hydrogenated at 200° C under a hydrogen pressure of 100 kg/cm² for three days to give 7.7 g of squalane.

EXAMPLE 17

In a 300 ml autoclave were placed 20 g of 2,6,10,15,19,23-hexamethyltetracosane-10,15-diol, 40 ml of n-heptane, 0.4 ml of acetic acid and 0.4 g of 5% palladium on active carbon and the mixture was hydrogenated at 200° C under a hydrogen pressure of 100 kg/cm² for 15 hours to give squalane quantitatively.

EXAMPLE 18

This example was carried out in the same manner as in example 17 except that nickel diatomaceous earth was used in place of 5% palladium on carbon and 0.4 g of magnesium sulfate with 7 hydrated water was used in place of acetic acid and the same result was obtained.

What is claimed is:

1. A process for preparing squalane which comprises submitting,
  i. a compound having the formula (I):

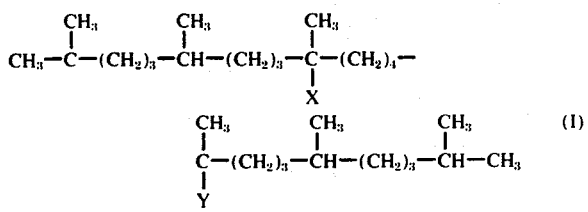

(I)

wherein X and Y represent hydroxy radicals or one of X and Y represents a hydroxy radical and the other represents a hydrogen atom, ii. a mixture of compounds of the formula (I), or a mixture of (iii) with squalane, to hydrogenolysis in the presence of a metal catalyst selected from the group consisting of nickel, cobalt, palladium, platinum, rhodium, iridium, ruthenium, osmium and rhenium and a compound thereof unsupported or supported on a carrier and in the presence of an acidic substance selected from the group consisting of organic carboxylic acids, Brønsted acids, Lewis acids, solid acids, and hydrogen salts of a strong acid and a weak base at a temperature of from about 100° to 300° C. under a hydrogen pressure of from about 20 to about 150 kg/cm².

2. The process for preparing squalane of claim 1 in which the hydrogenolysis is carried out in an organic carboxylic acid.

3. The process for preparing squalane of claim 1 in which the hydrogenolysis is carried out in an organic carboxylic acid together with an amount of a stronger acidic substance than said organic carboxylic acid, said amount being insufficient to prohibit the hydrogenolysis.

4. The process for preparing squalane of claim 1, wherein the hydrogenolysis is carried out in a hydrocarbon solvent.

5. The process for preparing squalane of claim 2, wherein the organic carboxylic acid is selected from the group consisting of acetic acid, propionic acid, lactic acid and isolactic acid.

6. The process of claim 1, wherein the catalyst is Pd.

7. The process of claim 1, wherein the catalyst is nickel.

8. The process of claim 2, wherein the acidic substance is acetic acid.

9. The process of claim 1, wherein the Bronsted acid is sulfuric acid.

10. The process of claim 1, wherein the Bronsted acid is hydrochloric acid.

11. The process of claim 1, wherein the solid acid is activated alumina.

12. The process of claim 1, wherein the salt of a strong acid and a weak base is magnesium sulfate.

* * * * *